(12) United States Patent
Wu et al.

(10) Patent No.: US 10,439,120 B2
(45) Date of Patent: Oct. 8, 2019

(54) THERMOELECTRIC MATERIAL, AND PREPARATION METHOD THEREFOR AND APPLICATION THEREOF

(71) Applicant: FUJIAN INSTITUTE OF RESEARCH ON THE STRUCTURE OF MATTER, CHINESE ACADEMY OF SCIENCES, Fujian (CN)

(72) Inventors: Liming Wu, Fujian (CN); Hua Lin, Fujian (CN); Ling Chen, Fujian (CN)

(73) Assignee: FUJIAN INSTITUTE OF RESEARCH ON THE STRUCTURE OF MATTER, CHINESE ACADEMY OF SCIENCES, Fujian (CN)

( * ) Notice: Subject to any disclaimer, the term of this patent is extended or adjusted under 35 U.S.C. 154(b) by 31 days.

(21) Appl. No.: 15/540,514

(22) PCT Filed: Dec. 29, 2014

(86) PCT No.: PCT/CN2014/095376
§ 371 (c)(1),
(2) Date: Jun. 28, 2017

(87) PCT Pub. No.: WO2016/106514
PCT Pub. Date: Jul. 7, 2016

(65) Prior Publication Data
US 2017/0373239 A1  Dec. 28, 2017

(51) Int. Cl.
*H01L 35/16* (2006.01)
*H01L 35/34* (2006.01)
(Continued)

(52) U.S. Cl.
CPC ............. *H01L 35/16* (2013.01); *H01L 35/34* (2013.01); *C01B 19/007* (2013.01);
(Continued)

(58) Field of Classification Search
CPC ......... H01L 35/16; H01L 35/34; G01N 27/04; G01N 23/00; C01G 5/006; C01D 17/003; C01B 19/007; C01P 2002/72
See application file for complete search history.

(56) References Cited

U.S. PATENT DOCUMENTS

2010/0193003 A1\*  8/2010  Lee .................. H01L 35/26
136/239

FOREIGN PATENT DOCUMENTS

JP            06120568 A   \*  4/1994

OTHER PUBLICATIONS

Li, Jing et al., CsAg5Te3. a new metal-rich telluride with a unique tunnel structure, J alloys and compounds, 218, pp. 1-4, 1995. (Year: 1995).\*

(Continued)

*Primary Examiner* — Jessee R Roe
*Assistant Examiner* — Rebecca Janssen
(74) *Attorney, Agent, or Firm* — Nath, Goldberg & Meyer; Jerald L. Meyer; Tanya E. Harkins

(57) ABSTRACT

The present application discloses a thermoelectric material, which contains $CsAg_5Te_3$ crystal material. At 700K, the thermoelectric material has an optimum dimensionless figure-of-merit ZT as high as 1.6 and a high stability, and the thermoelectric material can be recycled. The present application also discloses a method for preparing the $CsAg_5Te_3$ crystal material. The $CsAg_5Te_3$ crystal material is one-step synthesized by a high-temperature solid-state method, using a raw material containing Cs, Ag and Te, so that the high-purity product is obtained while the synthesis time is greatly shortened.

5 Claims, 4 Drawing Sheets

(51) Int. Cl.
  *C01B 19/00* (2006.01)
  *C01D 17/00* (2006.01)
  *C01G 5/00* (2006.01)
  G01N 23/00 (2006.01)
  G01N 27/04 (2006.01)
(52) U.S. Cl.
  CPC ........... *C01D 17/003* (2013.01); *C01G 5/006* (2013.01); *C01P 2002/72* (2013.01); *G01N 23/00* (2013.01); *G01N 27/04* (2013.01)

(56) References Cited

OTHER PUBLICATIONS

Encyclopedia Britannica, Arrhenius equation, https://www.britannica.com/science/Arrhenius-equation, 2017 (Year: 2017).*
Li, Jing, et al. "CsAg5Te3: a new metal-rich telluride with a unique tunnel structure." Journal of alloys and compounds 218.1 (1995): 1-4.

* cited by examiner

THERMOELECTRIC MATERIAL, AND PREPARATION METHOD THEREFOR AND
APPLICATION THEREOF

This is a National Phase Application filed under 35 U.S.C. 371 as a national stage of PCT/CN2014/095376, filed Dec. 29, 2014, the content of each of which is hereby incorporated by reference in its entirety.

TECHNICAL FIELD

The present application relates to a thermoelectric material, its preparation method and application, belonging to the field of material science.

TECHNICAL BACKGROUND

Under solid-state condition, thermoelectric materials can realize a direct interconversion of thermal and electrical energy by motion of internal carriers (electrons or holes) and is a green and environmental protective energy conversion material.

The work efficiency of thermoelectric devices is mainly determined by the performance of thermoelectric materials. The dimensionless figure-of-merit ZT is an important index to characterize the conversion efficiency of thermoelectric materials. The formula for calculating the dimensionless figure-of-merit is $$ZT=(S^2\sigma)T/\kappa$$

Where, S is the Seebeck coefficient; and $\sigma$ is the electric conductivity; and T is the absolute temperature; and $\kappa$ is the total thermal conductivity. $S^2\sigma$ is also known as power factor (abbreviated as PF), used for characterization of electrical properties of thermoelectric materials; and the total thermal conductivity K is comprised of two parts: lattice thermal conductivity (abbreviated as $\kappa_{lat}$) and electron thermal conductivity (abbreviated as $\kappa_{ele}$). In 1995, Li et al. reported a crystal material $CsAg_5Te_3$ (*J. Solid State Chem.* 1995, 218:1-4). In this paper, the synthesis of pure phase $CsAg_5Te_3$ adopts two-step method. Firstly, the binary phase $Cs_2Te$ is synthesized, and then the target product is obtained by reacting with Ag. The total reaction process is taken 10 days.

SUMMARY OF THE INVENTION

According to an aspect of the present application, a thermoelectric material with a dimensionless figure-of-merit ZT(700K) of 1.6 is provided. The thermoelectric material contains $CsAg_5Te_3$ crystal material. The $CsAg_5Te_3$ crystal material is at least one selected from the $CsAg_5Te_3$ crystal material prepared by any method provided in the present application, or the $CsAg_5Te_3$ crystal material prepared by other methods.

Preferably, the thermoelectric material is composed of the $CsAg_5Te_3$ crystal material.

The framework structure of $CsAg_5Te_3$ crystal material is formed by Ag and Te. It has three-dimensional channel structure and Cs is located in three-dimensional channel According to another aspect of the present application, a method for preparing $CsAg_5Te_3$ crystal material is provided. Using the method, $CsAg_5Te_3$ crystal material product with high purity is one-step synthesized, and synthesis time is greatly shortened.

The method for preparing $CsAg_5Te_3$ crystal material comprises that $CsAg_5Te_3$ crystal material is obtained by placing a raw material containing cesium element, silver element and tellurium element under a vacuum condition and using high temperature solid phase method.

Preferably, the mole ratio of cesium element, silver element and tellurium element in the raw material is Cs:Ag:Te=1:4.9-5.1:2.9-3.1.

More preferably, the mole ratio of cesium element, silver element and tellurium element in the raw material is Cs:Ag:Te=1:5:3.

Preferably, in the raw material, the silver element is from silver elementary substance; and the cesium element is from cesium elementary substance; and the tellurium element is from tellurium elementary substance. More preferably, in the raw material, silver elementary substance is located between cesium elementary substance and tellurium elementary substance.

Preferably, the condition of high temperature solid phase method is that the raw material is kept in a temperature range from 750° C. to 950° C. for no more than 48 hours.

Preferably, the condition of high temperature solid phase method is that the raw material is kept in a temperature range from 800° C. to 900° C. for no more than 24 hours.

As a preferred embodiment, the method for preparing $CsAg_5Te_3$ crystal material includes at least steps as follows:

a) placing cesium elementary substance, silver elementary substance and tellurium elementary substance in sequence in a vessel;

b) after vacuumizing and sealing, keeping the vessel in a temperature range from 750° C. to 950° C. for no more than 48 hours to obtain the $CsAg_5Te_3$ crystal material. Preferably, in step a), the cesium elementary substance does not contact with the tellurium elementary substance.

According to another aspect of the present application, a method for preparing a densified bulk thermoelectric material is provided, wherein the densified bulk thermoelectric material is obtained by hot-pressing sintering of the $CsAg_5Te_3$ crystal material obtained using any of the above-mentioned method; which is that the $CsAg_5Te_3$ crystal material is kept in a temperature range from 400° C. to 500° C. and in a pressure range from 60 MPa to 110 MPa for not less than 30 min to the obtain densified bulk thermoelectric material.

Preferably, the time of hot-pressing sintering is in a time range from 30 min to 90 min According to another aspect of the present application, a thermoelectric material is provided. At 700K, the thermal conductivity of the thermoelectric material can reach 0.19 W/m·K, and the electric conductivity can reach 53 S/cm, and the Seebeck coefficient can reach 295 μV/K, and the optimum dimensionless figure-of-merit ZT can reach 1.6. Meanwhile, the thermoelectric material has a high stability and can be recycled for many times.

The thermoelectric material contains $CsAg_5Te_3$ crystal material; and the weight percentage content of the $CsAg_5Te_3$ crystal material prepared by any of the above-mentioned method in total $CsAg_5Te_3$ crystal material contained in thermoelectric material ranges from 0 wt % to 100 wt %. Preferably, the weight percentage content of the $CsAg_5Te_3$ crystal material prepared by any of the above-mentioned method in total $CsAg_5Te_3$ crystal material contained in thermoelectric material is greater than 0 wt %. More Preferably, the weight percentage content of the $CsAg_5Te_3$ crystal material prepared by any of the above-mentioned method in total $CsAg_5Te_3$ crystal material contained in thermoelectric material is 100 wt %.

The thermoelectric material contains $CsAg_5Te_3$ crystal material prepared by any of the above-mentioned method and/or the densified bulk thermoelectric material prepared by any of the above-mentioned method.

Preferably, the thermoelectric material is composed of $CsAg_5Te_3$ crystal material prepared by any of the above-mentioned method and/or the densified bulk thermoelectric material prepared by any of the above-mentioned method.

According to another aspect of the present application, a thermoelectric converter is provided. The thermoelectric converter contains $CsAg_5Te_3$ crystal material. Preferably, the weight percentage content of the $CsAg_5Te_3$ crystal material prepared by any of the above-mentioned method in total $CsAg_5Te_3$ crystal material contained in thermoelectric converter ranges from 0 wt % to 100 wt %. Preferably, the weight percentage content of the $CsAg_5Te_3$ crystal material prepared by any of the above-mentioned method in total $CsAg_5Te_3$ crystal material contained in thermoelectric converter is greater than 0 wt %. More Preferably, the weight percentage content of the $CsAg_5Te_3$ crystal material prepared by any of the above-mentioned method in total $CsAg_5Te_3$ crystal material contained in thermoelectric converter is 100 wt %.

According to another aspect of the present application, a thermoelectric converter is provided. The thermoelectric converter contains $CsAg_5Te_3$ crystal material prepared by any of the above-mentioned method and/or the densified bulk thermoelectric material prepared by any of the above-mentioned method.

The advantages of the present application include at least:

(1) At 700K, the thermal conductivity of the thermoelectric material provided in the present application can reach 0.19 W/m·K, and the electric conductivity can reach 53 S/cm, and the Seebeck coefficient can reach 295 μV/K, and the optimum dimensionless figure-of-merit Li can reach 1.6.

(2) The thermoelectric material provided in the present application has high stability and can be recycled for many times.

(3) The method for preparing $CsAg_5Te_3$ crystal material provided in the present application is a one-step synthesis method, which can greatly reduce the synthesis time and obtain the product with high purity at the same time.

DETAILED DESCRIPTION OF THE EMBODIMENT

The present application will be further described by combining with Examples. It should be understand that these Examples are only used to illustrate the present application and not to limit the scope of the present application.

In the Examples, the X ray powder diffraction analysis of the samples were determined using a D/MAX2500 X-ray Diffractometer of Rigaku Corporation, with Cu target, Kα radiation source ($\lambda$=0.154184 nm).

The thermal conductivities were measured on a LFA427 thermal conductivity meter of German Netzsch.

The electric conductivities and Sebecke coefficients were measured using a ZEM-3 thermoelectric evaluation system of the Japanese ULAC-RIKO, Inc.

The hot pressing sintering was carried out in ZTY-15-20 hot pressing sintering furnace of Shanghai Chenxin Electric Furnace Co., LTD.

In the Examples, cesium elementary substance was a liquid cesium with purity of 99.98% purchased from Alfa Aesar (China) Chemical Co. LTD.; and silver elementary substance was a silver powder with purity of 99.999% purchased from Sinopharm Chemical Reagent Co., LTD.; and tellurium elementary substance was a tellurium block with purity of 99.999% purchased from Sinopharm Chemical Reagent Co., LTD.

Example 1 Preparation of Samples 1 Powder to 4 Powder

The liquid cesium, silver powder and tellurium block were placed in a quartz reaction tube in sequence. After being vacuumized to $10^{-2}$ Pa, the quartz reaction tube was sealed with oxyhydrogen flame and then placed in a high temperature furnace. And then it spent 10 hours for increasing the temperature of the high temperature furnace from room temperature to the solid melting temperature. After keeping the temperature at the solid melting temperature for a solid melting time, the temperature was naturally cooled to room temperature, grinding to obtain the $CsAg_5Te_3$ crystal material powder samples.

The relationship of number of Samples with molar ratios in the raw material, solid melting temperatures and solid melting times were shown in Table 1.

TABLE 1

| Samples | Molar Ratio in the raw material | Solid Melting Temperature (° C.) | solid melting time (h) |
|---|---|---|---|
| 1 Powder | Cs:Ag:Te = 1:5:3 | 850 | 20 |
| 2 Powder | Cs:Ag:Te = 1:4.9:2.9 | 950 | 12 |
| 3 Powder | Cs:Ag:Te = 1:5.05:3.05 | 900 | 24 |
| 4 Powder | Cs:Ag:Te = 1:5.1:3.1 | 750 | 48 |

Example 2 Structural Characterization of the Samples 1 Powder to 4 Powder

Figure 1:
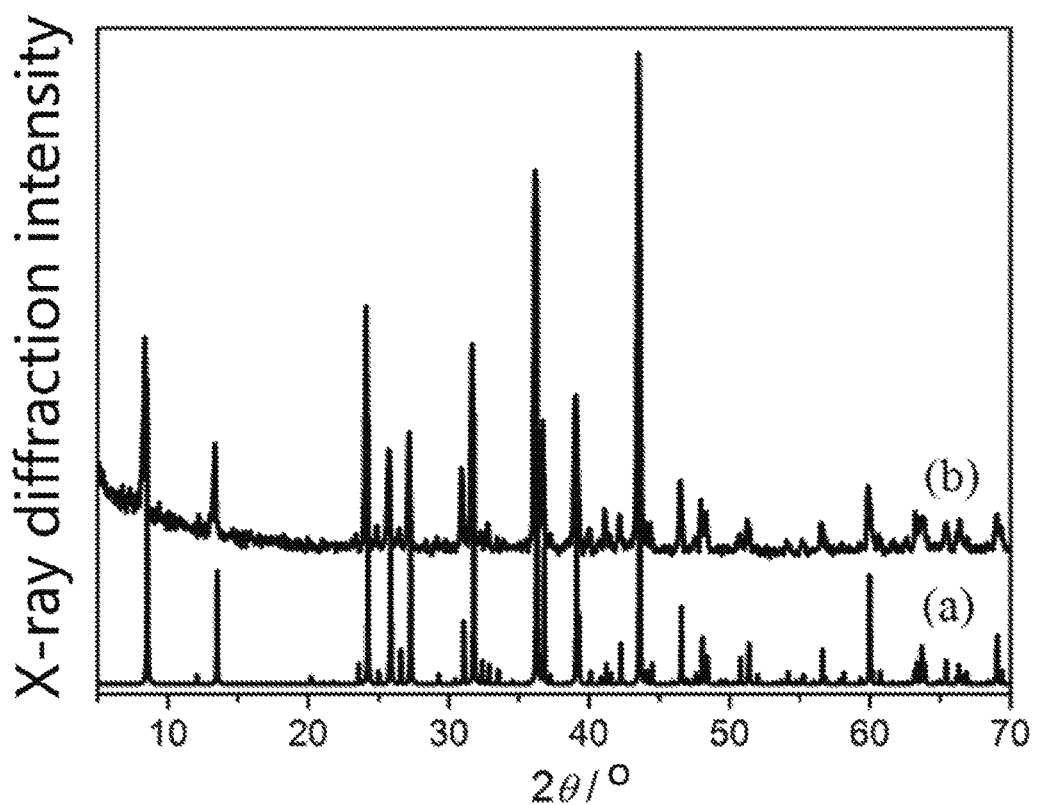
FIG. 1 is XRD powder diffraction spectrum of Sample 1 powder: (a) is the theoretical powder X-ray diffraction spectrum of $CsAg_5Te_3$; (b) is the powder X-ray diffraction spectrum of the Sample 1 powder obtained by experimental measure.

The X-ray powder diffraction analysis (XRD) of Samples 1 Powder to 4 Powder were determined. The results indicated that Samples 1 Powder to 4 Powder prepared in Example 1 all were $CsAg_5Te_3$ crystal samples with high purity. The typical XRD spectrum was the XRD spectrum of Sample 1 Powder, which was shown in FIG. 1. In FIG. 1, (a) is the theoretical powder X-ray diffraction spectrum of $CsAg_5Te_3$ and (b) is the powder X-ray diffraction spectrum of the Sample 1 powder obtained by experimental measure.

It showed that the experimental spectrum was high consistent with the theoretical spectrum simulated from single crystal data, indicating that the sample prepared was with a very high purity. XRD spectra of Sample 2 Powder, Sample 3 Powder and Sample 4 Powder were similar to FIG. 1, which showed that each corresponding peak had the same peak position and the ±5% difference of peak intensity.

Example 3 Preparation of Densified Bulk Samples 1 to 4

The Samples 1 Powder to 4 Powder were put into a hot pressing sintering furnace respectively, to obtain the densified bulk samples, and the densified bulk samples were respectively recorded as Sample 1 to Sample 4. The relationship of number of Samples with the conditions of hot pressing sintering were shown in Table 2

TABLE 2

| Samples | Pressure (MPa) | Temperature (° C.) | Time (min) |
|---|---|---|---|
| 1 | 110 | 400 | 30 |
| 2 | 100 | 430 | 40 |
| 3 | 80 | 460 | 60 |
| 4 | 60 | 500 | 90 |

Example 4 Measurement of Thermoelectric Properties of Samples 1 to 4

The thermoelectric properties of Samples 1 to 4 obtained in Example 3 were measured us a thermoelectric evaluation system. The detailed process was as follows: cutting the densified bulk Samples 1 to 4 by hot pressing sintering into a disk with 10 mm diameter and 2 mm thickness, respectively, to be used in the measurement of thermal conductivity; and cutting the densified bulk Samples 1 to 4 into a cuboid of 2 mm×3 mm×10 mm, respectively, to be used in the measurement of Seebeck coefficient.

Figure 2:
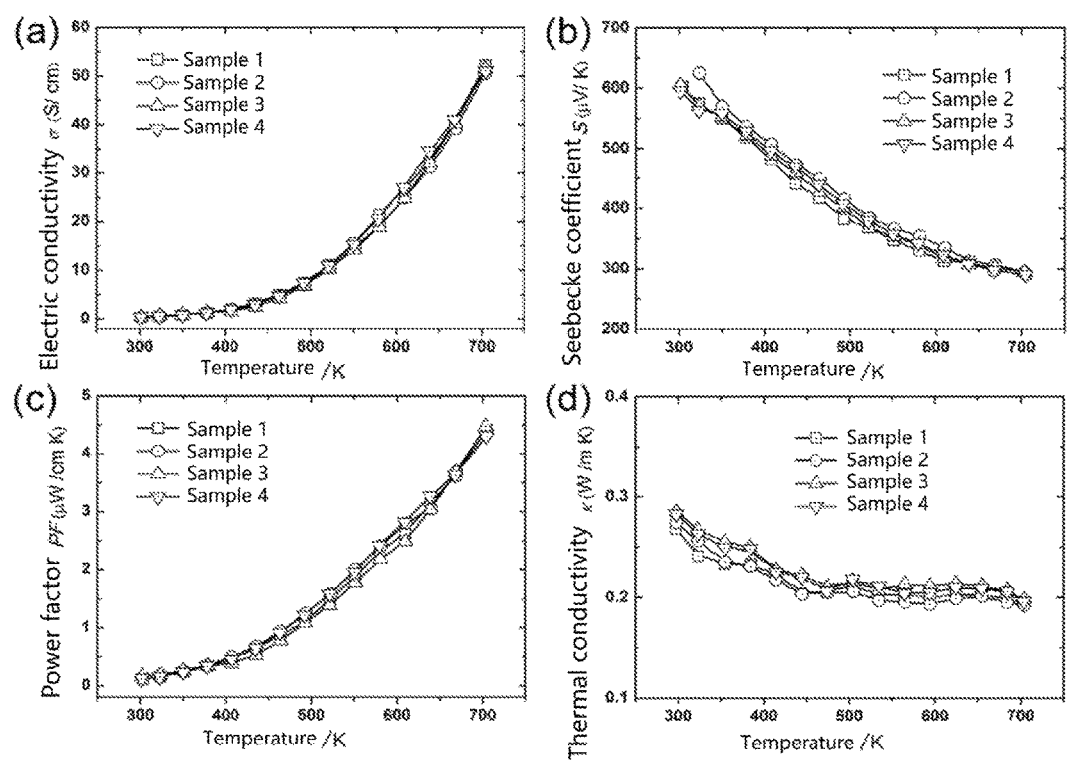
FIG. 2 is a graph showing the relationship of electrothermal transport properties to temperature of Samples 1 to 4: (a) shows the relationship of electric conductivity to temperature; (b) shows the relationship of Seebeck coefficient to temperature; (c) shows the relationship of power factor to temperature; (d) shows relationship of thermal conductivity to temperature.

The relationship of electrothermal transport properties to temperature of Samples 1 to 4 was shown in FIG. 2. And FIG. 2(*a*) had shown the relationship of electric conductivity to temperature; and FIG. 2(*b*) had shown the relationship of Seebeck coefficient to temperature; and FIG. 2(*c*) had shown the relationship of power factor to temperature; and FIG. 2(*d*) had shown relationship of thermal conductivity to temperature. It indicated that Samples 1 to 4 all have moderate electric conductivity and high Seebeck coefficient and the lowest thermal conductivity comparing with the similar thermoelectric materials which currently exist.

Figure 3:
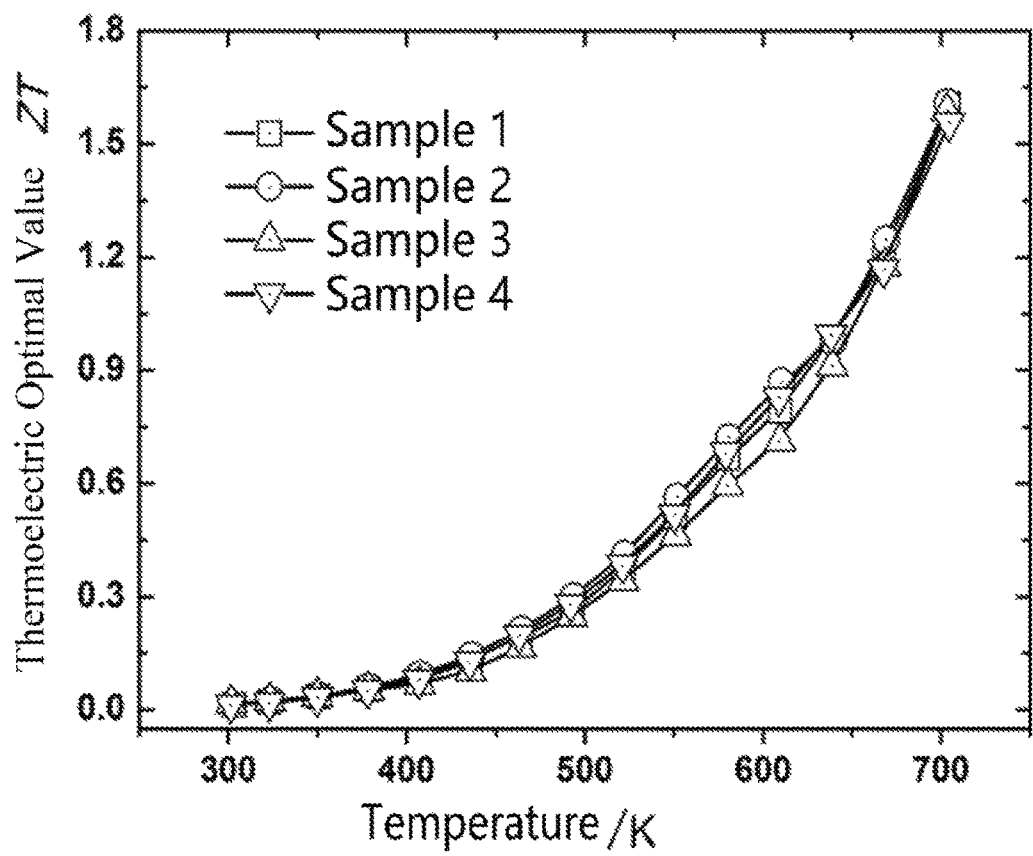
FIG. 3 is a graph showing the relationship of Dimensionless figure-of-merit to temperature of Samples 1 to 4.

The graph showing the relationship of Dimensionless figure-of-merit to temperature of Samples from 1 to 4 had been shown in FIG. 3. It indicated that at 700K, the optimum dimensionless figure-of-merit ZT could reach 1.6, which is the highest vale among polycrystal thermoelectric materials without doping modification which currently exist. The ZT of the thermoelectric material provided in the present application is expected to be improved through further optimization.

Example 5 Measurement Thermoelectric Properties of the Recycled Sample 1

The thermoelectric properties of the recycled Sample 1 were measured. The detailed process was as follows: cutting the densified bulk Sample 1 into a cuboid of 2 mm×3 mm×10 mm; and then placing the cuboid in the ZEM-3 thermoelectric evaluation system to in-situ measure for 3 times.

Figure 4:
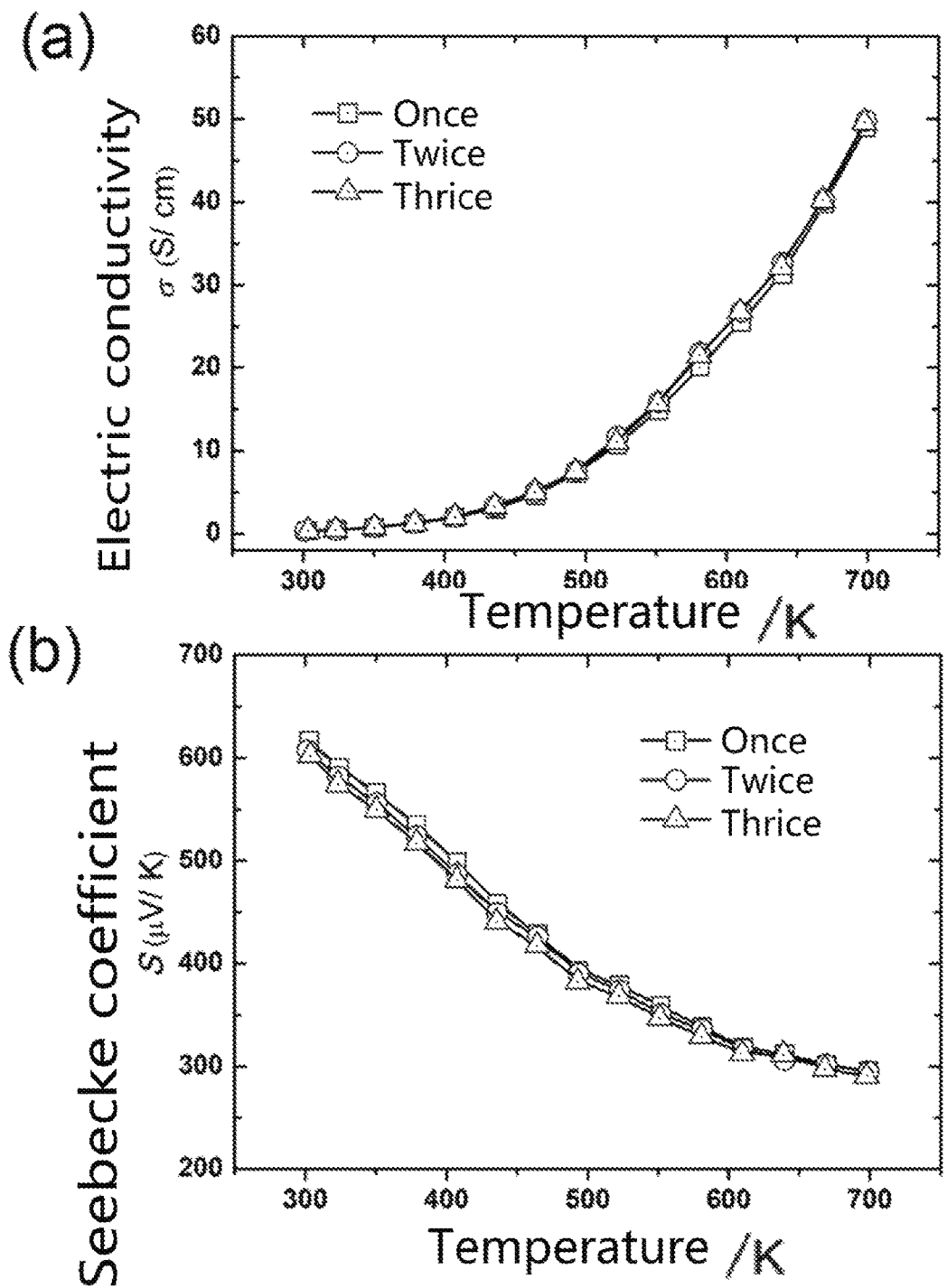
FIG. 4 is a graph showing the relationship of the electrical transport property to temperature of Sample 1 recycled for once, twice and three times: (a) shows the relationship of electric conductivity to temperature; (b) shows the relationship of Seebeck coefficient to temperature.

The relationship of the electrical transport property to temperature of Sample 1 had been shown in FIG. 4. And (a) had shown the relationship of electric conductivity to temperature; and (b) had shown the relationship of Seebeck coefficient to temperature. It indicated that the sample has high stability and recyclability.

It will be understood that the foregoing Examples are only some examples of the present application, rather than limit the present application in any form. Although the optimized examples of the present application are illustrated as above, they are not intended to limit the present application. In view of the instant disclosure, modifications or changes may be made by those skilled in the art without departing from the spirit and purview of the present application, and those modifications or changes are equivalent embodiments of the present application, falling into the scope of the appended claims.

The invention claimed is:

1. A method for preparing $CsAg_5Te_3$ crystal material, wherein $CsAg_5Te_3$ crystal material is obtained by placing raw materials containing cesium elementary substance, silver elementary substance and tellurium elementary substance under a vacuum condition, wherein the raw materials are kept in a temperature range from 750° C. to 950° C. for no more than 48 hours.

2. The method for preparing $CsAg_5Te_3$ crystal material according to claim 1, wherein the mole ratio of cesium elementary substance, silver elementary substance and tellurium elementary substance in the raw materials is Cs:Ag:Te=1:4.9-5.1:2.9-3.1.

3. The method for preparing $CsAg_5Te_3$ crystal material according to claim 1, wherein the mole ratio of cesium elementary substance, silver elementary substance and tellurium elementary substance in the raw materials is Cs:Ag:Te=1:5:3.

4. The method for preparing $CsAg_5Te_3$ crystal material according to claim 3, wherein in the raw materials, silver elementary substance is located between cesium elementary substance and tellurium elementary substance.

5. The method for preparing a densified bulk thermoelectric material, wherein the densified bulk thermoelectric material is obtained by hot-pressing sintering of the $CsAg_5Te_3$ crystal material obtained using the method according to claim 1, wherein the $CsAg_5Te_3$ crystal material is kept in a temperature range from 400° C. to 500° C. and in a pressure range from 60 MPa to 110 MPa for not less than 30 min to obtain the densified bulk thermoelectric material.

* * * * *